(12) United States Patent
Chou

(10) Patent No.: US 10,688,311 B2
(45) Date of Patent: Jun. 23, 2020

(54) MAGNETIC THERAPY DEVICES AND RELATED METHODS

(71) Applicant: Selfkaire, Inc., Encino, CA (US)

(72) Inventor: Kathy Chou, Irvine, CA (US)

(73) Assignee: SELFKAIRE, INC., Irvine, CA (US)

( * ) Notice: Subject to any disclaimer, the term of this patent is extended or adjusted under 35 U.S.C. 154(b) by 0 days.

(21) Appl. No.: 16/575,252

(22) Filed: Sep. 18, 2019

(65) Prior Publication Data
US 2020/0108266 A1    Apr. 9, 2020

Related U.S. Application Data

(60) Provisional application No. 62/740,764, filed on Oct. 3, 2018.

(51) Int. Cl.
*A61N 2/00* (2006.01)
*A61N 2/08* (2006.01)
*A61N 2/06* (2006.01)

(52) U.S. Cl.
CPC ............... *A61N 2/06* (2013.01); *A61N 2/004* (2013.01)

(58) Field of Classification Search
CPC .. A61N 2005/0644; A61N 2/00; A61N 2/002; A61N 2/008; A61N 2/02; A61H 2201/0207; A61H 2201/10
See application file for complete search history.

(56) References Cited

U.S. PATENT DOCUMENTS

| 4,691,693 A | 9/1987 | Sato |
| 6,001,055 A | 12/1999 | Souder |
| 7,082,871 B2 | 8/2006 | Schultz |
| 2013/0238061 A1* | 9/2013 | Ron Edoute ........... A61N 1/403 607/101 |

FOREIGN PATENT DOCUMENTS

| CN | 1984629 A | 6/2007 |
| CN | 201235059 Y | 5/2009 |
| DE | 102008055885 B4 | 4/2011 |
| JP | 2016083181 A | 5/2016 |

(Continued)

OTHER PUBLICATIONS

Google Search, "facial rollers," 5 pages [online], [retrieved on Aug. 6, 2019]. Retrieved from the Internet: <URL:https://www.google.com/search?q=facial+rollers&client=safari&hl=en-us&prmd=sinv&source=lnms&tbm=isch&sa=X&ved=0ahUKEwj18vOimdfdAhUEOn0KHewPBsAQ_AUIEigC&biw=375&bih=635>.

(Continued)

*Primary Examiner* — Christine H Matthews
*Assistant Examiner* — Joshua Daryl D Lannu
(74) *Attorney, Agent, or Firm* — Klein, O'Neill & Singh, LLP

(57) ABSTRACT

The present disclosure provides a magnetic therapy device. The therapy device includes a body having a holding portion and a mounting portion. The holding portion is adapted to be held by a user for maneuvering the therapy device to access a treatment area on a skin of the user and the mounting portion is attached the holding portion. Further, the therapy device has at least one hollow pin mounted to the mounting portion. The at least one hollow pin encloses at least one magnet, with the magnetic field of the magnet extending outside of the hollow pin to impart magnetic flux onto a treatment area of a patient.

18 Claims, 8 Drawing Sheets

(56) References Cited

FOREIGN PATENT DOCUMENTS

| | | |
|---|---|---|
| KR | 101468058 B1 | 12/2014 |
| WO | 2000057832 A1 | 10/2000 |

OTHER PUBLICATIONS

ReFa USA, "USA Official Website," 2019, 4 pages [online], [retrieved on Aug. 6, 2019]. Retrieved from the Internet: <URL:https://www.refausa.com/>.

International Search Report and Written Opinion on related international application No. PCT/US2019/052842 from Authorized Officer S. Denisyuk dated Dec. 19, 2019 (7 pages).

* cited by examiner

MAGNETIC THERAPY DEVICES AND RELATED METHODS

CROSS-REFERENCE TO RELATED APPLICATIONS

This application claims the benefits of U.S. Provisional Patent Application Ser. No. 62/740,764, filed on Oct. 3, 2018, the entire contents of which is expressly incorporated herein by reference.

STATEMENT RE: FEDERALLY SPONSORED RESEARCH/DEVELOPMENT

Not Applicable

BACKGROUND

The current devices, systems and methods relate to therapy devices. In particular, the devices, systems, and methods relate to therapy devices with at least one magnet.

When people age, skin tissue and lymph nodes may retain fluid. Unfortunately, such condition causes the skin to look unappealing.

As such, there is a need in the art for an improved method and device for rejuvenating skin tissue.

BRIEF SUMMARY

A handheld device for rejuvenating skin tissue is disclosed. The handheld device provides three magnets which produce a magnetic field. The magnetic field penetrates the skin tissue of a body part to rejuvenate or treat the skin tissue. The magnets may have magnetic fields which intersect and the magnetic fields at the intersection may penetrate the skin tissue of the body part being treated to rejuvenate the skin tissue. By way of example and not limitation, the device may help to detoxify tissue to drain fluids in the tissue, improves lymphatic drainage and compresses the tissues.

More particularly, a magnetic therapy device for treating a body part is disclosed. The device may comprise a body, first, second and third pins and first, second and third magnets. The body may include a holding portion for gripping by a user's hand and a mounting portion attached to the holding portion. The first, second and third pins may be attached to the mounting portion. The first, second and third pins may extend away from the holding portion of the body. The first pin may define a first cavity. The second pin may define a second cavity. The third pin may define a third cavity. The first magnet may be disposed within the first cavity of the first pin. The second magnet may be disposed within the second cavity of the second magnet. The third magnet may be disposed within the third cavity of the third pin.

The polarities of the first, second and third magnets may be oriented in the same direction and may be parallel to each other. Alternatively, the polarities of the first, second and third magnets may be oriented at skewed angles with respect to each other. The magnetic north poles of the first, second and third magnets may be directed in the same direction.

The first, second and third magnets may be equidistantly spaced apart from each other about 1 to 3 inches.

The pins may be fabricated from surgical steel or titanium.

The device may further comprise a heater disposed within the body for providing heat to the surfaces of the pins that contact the body part being treated; a vibrator disposed within the body for providing vibration to the body part being treated; and a battery disposed with the body and electrically connected to the heater and the vibrator to power the heater and the vibrator. Additionally or alternatively, the device may further comprise a cooler disposed within the body for drawing heat away from the surfaces of the pins that contact the body part being treated.

The pins may comprise rollers to allow for easier traversal of the pins over the surface of the body part being treated. The body may have an upper dome shaped surface to ergonomically interface with a palm of a user.

The device may further comprise a neck portion which connects the holding portion and the mounting portion, the neck portion being narrower compared to the holding portion and the mounting portion, the neck portion being sufficiently narrow so that a person's index and middle fingers can be placed on opposed sides of the neck portion.

The pins may be removably attachable to the mounting portion to interchange the magnets disposed in the cavities of the pins with stronger or weaker magnets. Springs may be disposed within the cavities of the pins to stabilize the magnets within the cavities of the pins.

In another aspect, a method of treating a body part with a magnetic field is disclosed. The method may comprise the steps of touching two pins of a magnetic therapy device on a surface of a body part being treated; allowing two magnetic fields of two magnets of the two pins which intersect to penetrate a location of the surface of the body part being treated at the same time; and moving the intersecting magnetic field over the surface of the body part being treated.

In the method, the moving step may further comprise the step moving the intersecting magnetic field in a FIG. 8 motion on the surface of the body part being treated.

The method may further comprise the step of allowing a weight of the device to apply pressure to the surface of the body part being treated.

In the method, the moving step may be performed for 15 minutes.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
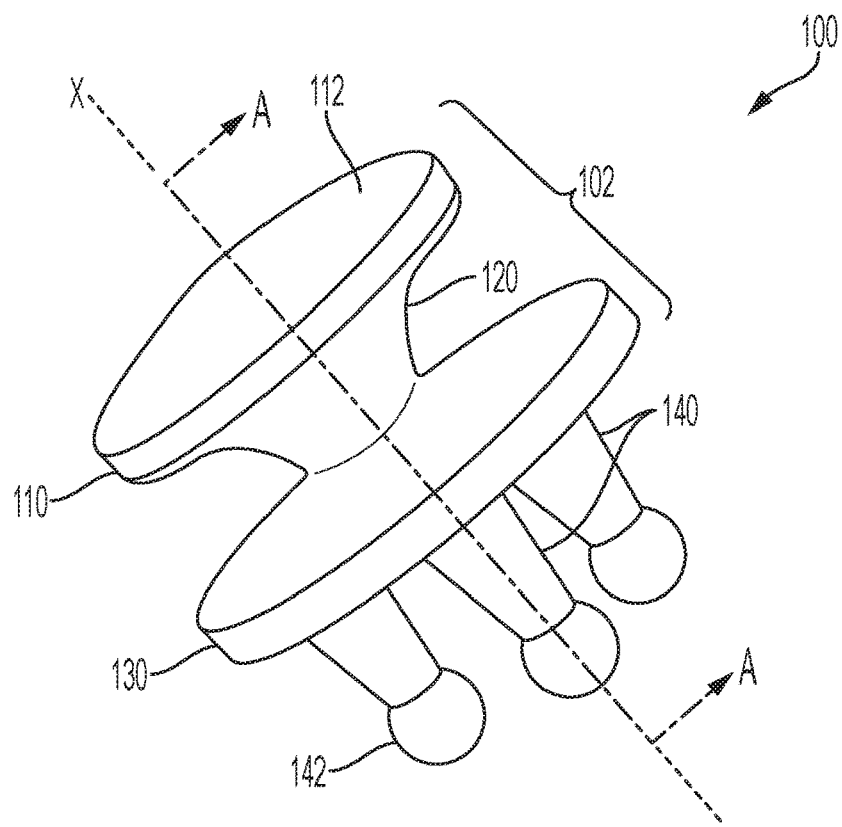
FIG. 1 shows a perspective view of a first embodiment of a magnetic therapy device.

FIG. 1 illustrates a perspective view of an exemplary embodiment of a magnetic therapy device 100. The magnetic therapy device 100 is hereinafter referred as a therapy device 100. The therapy device 100 may be applied over a treatment area to enhance lymphatic circulation and blood circulation within a patient's body. The term 'treatment area' refers to a portion of outer skin of an individual.

The therapy device 100 may include a body 102 and three hollow pins 140. However, the therapy device 100 may have only one hollow pin 140 or a higher number of hollow pins 140 than at least one hollow pin. The body 102 may include a holding portion 110, a neck portion 120, and a mounting portion 130. The neck portion 120 may be between the holding portion 110 and the mounting portion 130. The hollow pins 140 may be attached to the mounting portion 130. For explanation purposes, orientation of the therapy device 100 may be understood with the holding portion 110 being a top side, or proximal direction, and the hollow pins 140 being a bottom side, or distal direction, as understood along a device axis X. The usage of top side and bottom side orientation are merely for explanatory reasoning and are not limiting to positioning of the therapy device 100 in usage.

Figure 2:
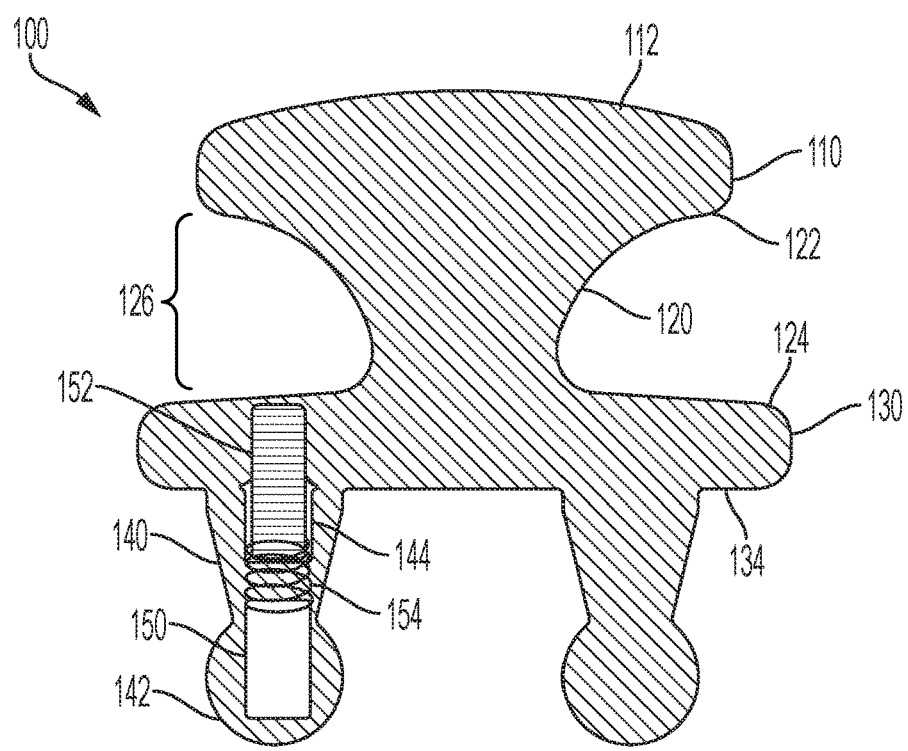
FIG. 2 shows a cross-sectional side view of the magnetic therapy device of FIG. 1 taken along line A-A.

As shown in FIG. 1, the holding portion 110 and the neck portion 120 may be sized and shaped for holding by a user. The holding portion 110 may have a cylindrical shape or disc shape when viewed from a top view. Also, the holding portion 110 may have a top surface 112 that is a convex or domed surfaced with a radius of curvature as shown in FIG. 2. The radius of curvature of the top surface 112 may be approximately 1 inch to 24 inches. More preferably, the radius of curvature may be approximately 2 inches to 6 inches. In one example, the radius of curvature may be 2 inches. The diameter of the cylindrical shape of the holding portion 110 may be greater than a thickness of the holding portion 110. The distance between the holding portion 110 and the mounting portion 130, or the length of the neck portion 120, may be approximately 0.5 inches to 3 inches. More preferably, the distance may be approximately 0.5 inches to 1.5 inches. In one example, the distance may be approximately 1 inch.

However, it is also conceived that alternative geometric shapes as viewed from a top view may be utilized for the holding portion 110. For example, the holding portion 110 may define a square, a rectangle, a triangle, or a star, among other geometric shapes. The geometric shape may be chosen for the user depending on the size of the therapy device.

The top surface 112 may have a convex or domed feature as shown in FIG. 2. In some embodiments where the therapy device 100 is sized to fit in a palm of a user, with the user gripping around the holding portion 110 with their fingers, the provision of a convex surface may allow for comfortable placement in the palm. The diameter of the holding portion 110 of the therapy device may be approximately 0.5 inches to 5 inches. More preferably, the distance may be approximately 1 inch to 3.5 inches. In one example, the distance may be approximately 3 inches. In some embodiments where the therapy device 100 is sized for grasping by three fingers, with two fingers below the holding portion 110 and a thumb finger over the top surface 112, the convex surface may provide a comfortable surface for the thumb finger.

However, it is also conceived that the top surface 112 may be have a concave, or inwardly domed, feature. This may be especially useful in embodiments sized for grasping by three fingers with two fingers below the holding portion 110 and the thumb finger over the top surface 112. In this case, the thumb finger of the user may have a natural resting spot on in the depression formed in the top surface 112 by the concave feature. The diameter of the holding portion 110 of the therapy device may be approximately 0.5 inches to 5 inches. More preferably, the distance may be approximately 1 inch to 3 inches. In one example, the distance may be approximately 1.5 inches.

The neck portion 120 may extend from a bottom side of the holding portion 110. The neck portion 120 may have a first end 122 attached to the holding portion and an opposed second end 124 attached to the mounting portion 130. The first end 122 may have a larger cross-section diameter than a cross-sectional diameter of the second end 124, such that the neck portion 120 tapers inwardly from the holding portion 110 to the mounting portion 130. The second end 124 may taper down to a first diameter and then flare outwards to a second diameter where it attaches to the mounting portion 130, such as would be understood with filleting or rounding to prevent a sharp edge where the neck portion 120 meets the mounting portion 130. The second end 124 may attach to the mounting portion 130 on a top surface of the mounting portion 130. The holding portion 110, the neck portion 120, and the mounting portion 130 may be fabricated from a unitary material or by three separate pieces that are attached to each other. The mounting portion 130 may have a diameter larger than the cross-sectional diameter of the second end 124. As such, the neck portion 120 may define a groove between the holding portion 110 and the mounting portion 130. Additional description about user ergonomics and gripping of the therapy device 100 is discussed below with regards to methods of use.

It is also conceived that alternative cross-sectional geometric shapes as viewed from a top view may be utilized for the neck portion 120. For example, the neck portion 120 may define a square, a rectangle, a triangle, or a star, among other geometric cross-sectional shapes. These geometric shapes may still be understood with the tapering inwardly contour of the neck portion 120 from the first end 122 to the second end 124. The geometric shape may be chosen based on ergonomic needs of the user depending on the size of the therapy device.

The neck portion 120 may include a tapering region 126 tapering inwardly from 50% up to 90% of the length between the holding portion 110 and the mounting portion 130 before flaring outward to attach to the mounting portion 130 as shown in FIG. 2. The tapering inwardly may reduce the cross-sectional diameter of the neck portion 120 from 30% up to 80% at an intermediary location between the holding portion 110 and the mounting portion 130 relative to the first end 122 or the holding portion 110.

The geometric features of the holding portion 110 and the neck portion 120 may be sized and shaped for the user based on the dimensions of the holding portion 110 and the neck portion 120. Aspects of the embodiment may include where the holding portion 120 has a diameter smaller than approximately two inches, the user may grip the therapy device by having two of their index, middle, ring, and pinkie fingers in the groove defined by the neck portion 120. The user may then also place their thumb finger on the top surface 112 of the holding portion 110. Alternatively, in embodiments where the holding portion 110 has a diameter larger than approximately two inches, the user may grip the therapy device 100 by using all five fingers to grip around the holding portion 110 and the groove of the neck portion 120. The holding portion may have a top surface 112, which has a convex curvature to fit a user's palm concave shape when gripping objects. By way of example and not limitation, the convex curvature may have a contoured shape with a radius of curvature with a radius from approximately 1 inch to 24 inches. More preferably, the radius of curvature may be approximately 2 inches to 6 inches. In one example, the radius of curvature may be 2 inches. The convex curvature of the holding portion 110 and the neck portion 120 may allow for fine control and maneuvering of the therapy device 100.

Extending from the second end 124 of the neck portion 120 is the mounting portion 130. The mounting portion 130 may have a top surface 132 and a bottom surface 134. The second end 124 may meet the mounting portion 130 at the top surface 132 of the mounting portion 130. The mounting portion 130 may have a cross-sectional diameter larger than the cross-sectional diameter of the second end 124. The mounting portion 130 may have a larger cross-sectional diameter than the cross-sectional diameter of the holding portion 110. That is, the diameter of the holding portion 110 of the therapy device may be approximately 0.75 inches to 5.5 inches. More preferably, the distance may be approximately 1 inch to 4 inches. In one example, the distance may be approximately 2 inches.

It is contemplated that alternative geometric shapes as viewed from a top view may be utilized for the mounting portion 130. For example, the mounting portion 130 may define a square, a rectangle, a triangle, or a star, among other geometric shapes. The geometric shape of the mounting portion 130 may be different from the geometric shape of the holding portion 110. A maximum cross-sectional width or chord of the mounting portion 130 with an alternative geometric shape may be greater than a maximum cross-sectional width or chord of the holding portion 110. That is, when viewed from the top, the mounting portion 130 may have an area larger than the holding portion 110.

The holding portion 110, the neck portion 120, and the mounting portion 130 may be made of one or more materials sufficient for required structural stability and rigidity of the therapy device 100. It is contemplated the holding portion 110, the neck portion 120, and the mounting portion 130 may be made of a material such as but not limited to a metallic material, a composite material, a non-metallic material (e.g., plastic, carbon filber) or any other material, as per design feasibility and requirement. The holding portion 110, the neck portion 120, and the mounting portion 130 may be made from metal, such as steel, including stainless steel or surgical steel, titanium, or aluminum, plastic, or a composite, such as carbon fiber for lightweight. The different portions may be made of different materials in various combinations. For example, the mounting portion 130 may be made from a metal and the neck portion 120 and the mounting portion 130 may be made from plastic for comfort and ease of gripping for the user. Additionally, at least one of the holding portion 110, the neck portion 120, and the mounting portion 130 may have a coating or cover. The cover may be an elastomer or polymer for comfort and ease of gripping for the user.

The mounting portion 130 may be steel, such as stainless steel or surgical steel. The mounting portion 130 made of steel may then be sized and shaped to limit the magnetic field towards the user or operator of the therapy device 100.

At the bottom surface of the mounting portion 130, at least one hollow pin 140 may be attached the mounting portion 130 by way of a screw member 152. In the exemplary embodiment of FIGS. 1-4, the therapy device 100 may have three hollow pins 140. However, in other embodiments, fewer or more hollow pins may be provided on the therapy device 100.

FIG. 1 illustrates that the at least one hollow pin 140 may include a contact portion 142 for positioning over a treatment area of the patient. Furthermore, the contact portions 142 at the ends of each of the hollow pins 140 may be shaped in order to provide massaging effect to the patient during use of the therapy device 100. The hollow pins 140 may have a tapered upper portion and the contact portion 142, which may be spherical in shape at the end of the hollow pin. Alternative shapes for the tapered upper portion may also be envisioned, such as a cylindrical, non-tapered upper portion, square, rectangular, triangular, or other suitable shapes. The hollow pin 140 may have a diameter ranging from approximately 0.25 inches to 1.5 inch. More specifically, the hollow pin 140 may have a diameter from approximately 0.25 inches to 1 inch. In one example, the hollow pin 140 may have a diameter of approximately 0.5 inches. The hollow pin 140 may have a length, including the contact portion 142, from approximately 0.5 inches and 5 inches. More specifically, the length may be from approximately 1 inch and 4 inches. The length may be approximately 1.5 inch. The spherical shape of the contact portion 142 may be beneficial for allow for smooth gliding over top of clothing of the patient without catching or digging into the clothing. Alternative end shapes for the contact portion 142 may be envisioned, such as a hemispherical shape, a flat surface, a cylindrical shape arranged perpendicular to the upper portion of the hollow pin, or a partial ellipsoid shape. The contact portion 142 may be a smooth-curved surface so it does not prick the treatment area during use of the device 100.

Figure 3:
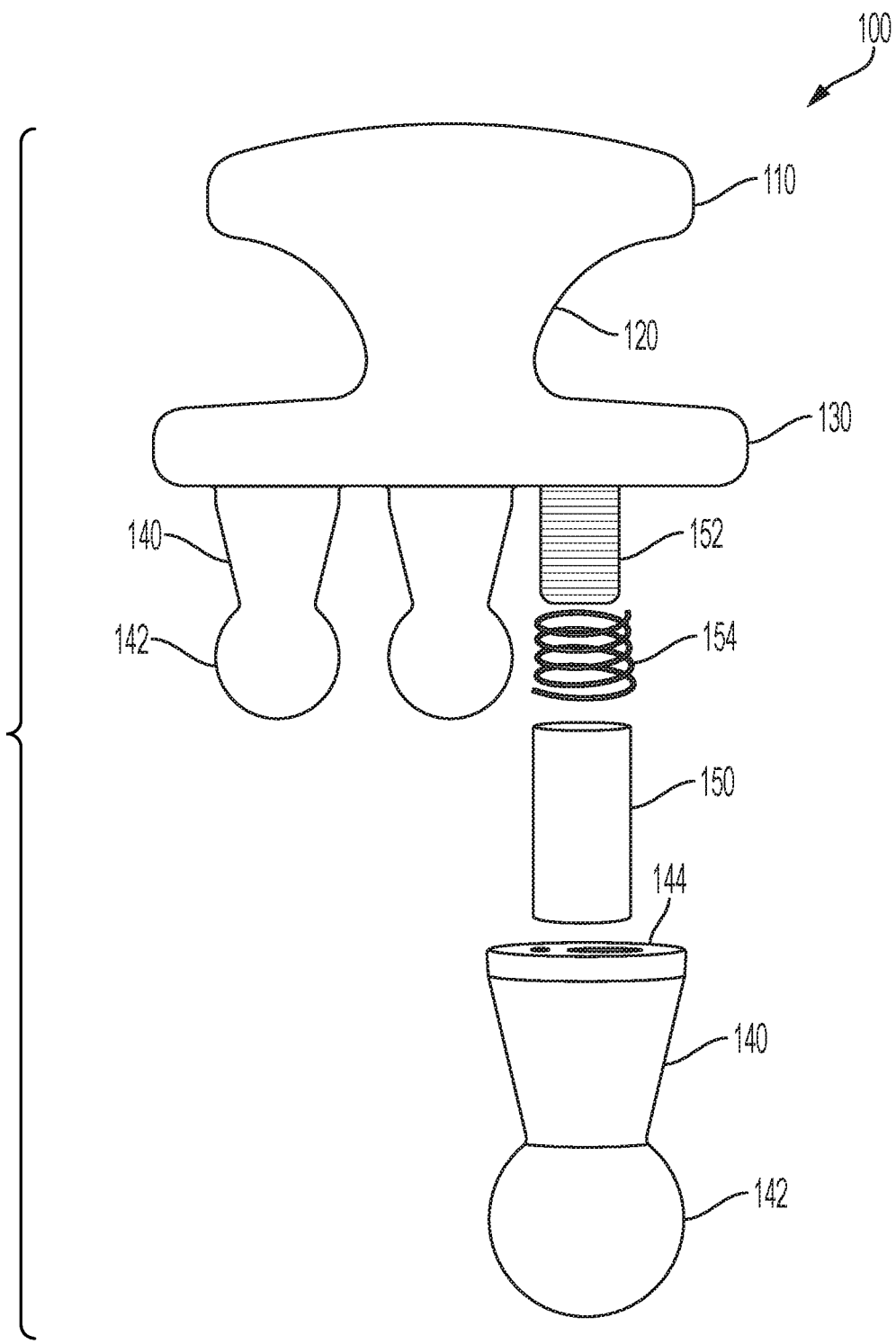
FIG. 3 shows a partial exploded side view of the magnetic therapy device of FIG. 1.

As shown in FIGS. 2 and 3, the hollow pin 140 may have a bore hole 144. FIG. 2 illustrates that the bore hole 144 may enclose a magnet 150, which is configured to provide a magnetic field extending outside of the hollow pin 140 for usage with the patient. As such, the magnet 150 is adapted to impart a magnetic flux onto the treatment area, during contact of the one or more hollow pins 140 with the treatment area for curing. The magnetic flux transferred to the treatment area, from the one magnet 150, promotes lymphatic tissue circulation within the body of the patient, thereby providing therapy on the treatment area by regulating toxins in the treatment area. It is also contemplated that more than one magnet 150 may be provided in each bore hole 144 of the hollow pins 140 to provide the desired magnet dimensions and magnetic field. It is contemplated that the magnet may be cylindrical, spherical, rectangular, or other geometric shapes as needed.

The magnet 150 may be a permanent magnet of one of a rare earth magnet, such as neodymium iron boron or samarium cobalt, alnico, ferrite, or ceramic magnets. The magnet 150 may be enclosed in the hollow pin in one of a variety of orientations. In some embodiments, the magnet 150 having a north pole and a south pole may be arranged north-south vertically aligned with the top-bottom orientation of the hollow pin 140 or the therapy device 100 along the device axis X as shown in FIG. 1. The magnet may be arranged with either the north pole or the south pole towards the end of the contact portion. In some embodiments, the magnet 150 may be arranged horizontally, whereby the north-south alignment of the magnet may be perpendicular, or transverse, to the top-bottom orientation of the hollow pin 140 or the therapy device 100 along the device axis X. In some embodiments, the arrangement of the magnet 150 may be with a north-south alignment at an angle relative to the top-bottom orientation of the hollow pin 140 or the therapy device 100 along the device axis X. In embodiments of two or more hollow pins 140 with magnets 150, it is not necessary that all of the magnets have the same orientation. For example, a therapy device 100 may have a first hollow pin 140 with a vertically arranged magnet and a second hollow pin 140 with a horizontally arranged magnet.

The magnet 150 may be positioned in the hollow pin 140 at a minimum distance from the distal exterior of the contact portion 142 from approximately 0.05 inches to 1 inches. It is contemplated that the magnet 150 may be a rare earth magnet from a range of grades from N35 to N55. More specifically, the magnet 150 may have a grade from N35 and N48. In one example, the magnet 150 may have a grade of N35. It is also contemplated that the magnet 150 may be a Samarium Cobalt magnet from a range of grades from 16 to 32. More specifically, the magnet 150 may be from a range of grades from 20 and 28. In one example, the magnet 150 may have a grade of 24.

The use of the hollow pin 140 extending away from the mounting portion 130 may allow for flexibility in targeting intricately contoured treatment areas of the patient. By utilizing the hollow pin 140 and the contact portion 142, the contact portion 142 and the enclosed magnet 150 may be placed as close as possible to the intricately contoured areas of the patient. Such placement would not be possible with a larger, single piece design where the contour of the patient's body would prevent placement as near as with the smaller contact portion 142. As such, the size and shape of the contact portion 142 and the hollow 140 may be predetermined as needed for optimal placement with desired applications. The contact portion 142 may have a diameter ranging from approximately 0.25 inches to 1.5 inch. More specifically, the hollow pin 140 may have a diameter from approximately 0.25 inches to 1 inch. For example, the contact portion 142 may be of a small size, such as small than approximately 0.5 inches in diameter, for usage around the knee joint. In one example, the contact portion 142 may be approximately 0.5 inches in diameter. Alternatively, the contact portion 142 may be on a large size, such as greater than approximately 0.5 inches in diameter, for applications on less intricately contoured areas of the patient. In one example, the contact portion 142 may be approximately 0.75 inches in diameter.

As shown in FIG. 2, the fixation of the magnet 150 inside the hollow pin 140 uses a resilient member, or spring, 154 and a screw member 152.

Figure 4:
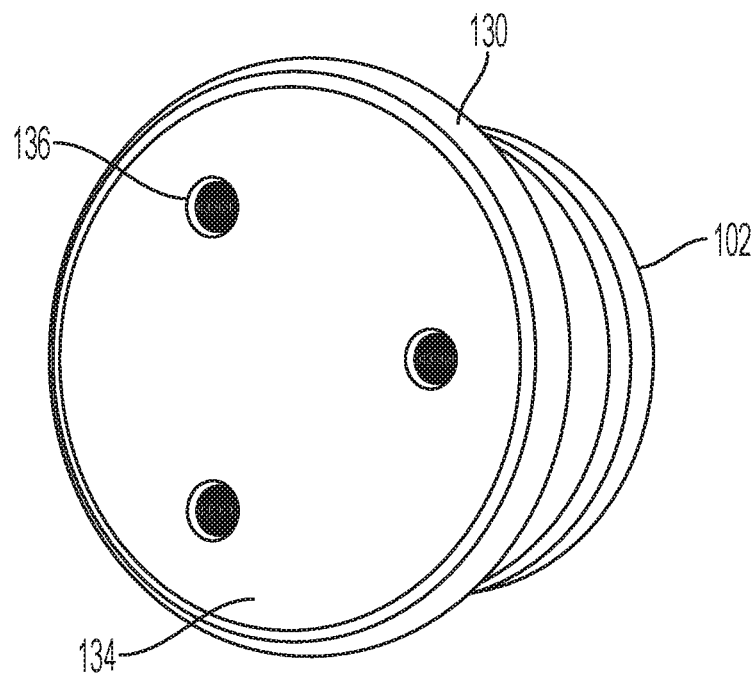
FIG. 4 shows a perspective bottom view of the mounting portion of the magnetic therapy device of FIG. 1.

The screw member 152 may extend from the mounting portion 130 and project below the bottom surface 134 of the mounting portion 130. As shown in FIG. 4, the bottom surface 134 of the mounting portion 130 may have mounting bores 136. These mounting bores 136 may be sized and threaded to correspond with the threads of the screw member 152. In this way, the screw members 152 may be screwed into the mounting portion 130 at set positions. The screw members 152 may then extend out from below the bottom surface 134 of the mounting portion 130. In this way, the screw members 152 may be exposed for engagement with the bore holes 144 of the hollow pins 140. The bore holes 144 may have matching threads for engagement with the screw members 152 for fastening of the hollow pins 140 to the screw members 152 and the mounting portion 130.

In some embodiments, the screw member 152 may be a dowel or fixing pin instead of a threaded screw member. The dowel or fixing pin may be fixed to the mounting portion 130 and the hollow pin 140 by means of adhesive or press fit. Alternatively, in some embodiments, the fixing pin may be a projection integrally formed on the mounting portion 130. Such an integrally formed projection may be a fixing pin or dowel for fixing to the bore hole 144 of the hollow pin 140 by means of adhesive or press fit.

In the bore hole 144 of the hollow pin 140, there may be provided a resilient member 154. The resilient member may be any of various resilient members, including but not limited to a coil spring, a deformable polymer, or a Belleville spring. In the assembled state where the hollow pin 140 is mated with the mounting portion 130, the resilient member 154 may be between the screw member 152 and the magnet 150. The resilient member 154 may be mounted to contact each of the screw members 152 and the magnet 150. The resilient member 154 may prevent misalignment of the magnet 150 within the hollow pins 140. This configuration of the resilient member 154 may allow the magnet 150 to maintain its position in the bore hole 144, irrespective of the orientation of the device 100 and the pressure applied on the device 100 during use. Additionally, the resilient member 154 ensures that the magnet 150 is located proximal to a tip of the hollow pins 140, so that predetermined magnetic flux emanating from the magnet 150 is transferred to the treatment area. The resilient member 154 may also act as a shock absorber, in the event an excessive force or sudden jolt is applied on the device 100 during use.

Figure 5:
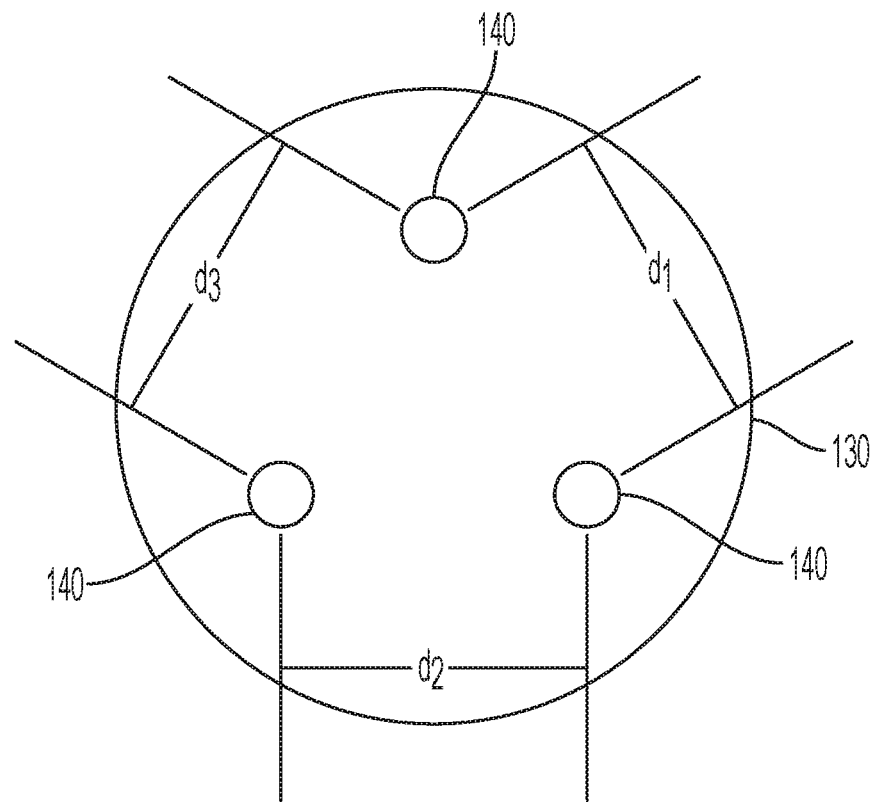
FIG. 5 shows a bottom view of the magnetic therapy device of FIG. 1.

FIG. 5 illustrates a bottom view of the therapy device 100 of FIG. 1, and an exemplary embodiment of a layout of the three hollow pins 140 of the therapy device 100. In one or more embodiments, the hollow pins 140 may be spaced equidistantly from one another with distances d1, d2, d3, wherein d1, d2, and d3 are equal in length to each other. However, the relative positioning of the hollow pins 140 may be variable based on needs.

It may be desired to have a variable distance arrangement of the hollow pins 140 wherein d1, d2, and d3 are not equal to each other. It may be desired to have a variable distance arrangement of the hollow pins 140 wherein two of d1, d2, and d3 are equal to each other but the third is not. For example, two hollow pins 140 could be spaced apart by a distance d1 to sufficiently span a lateral width of a muscle. The lateral width of a muscle may range from approximately 0.5 inches to 12 inches. More preferably, the distance d1 be predetermined from approximately 1 inch to 3 inches. In one example, the distance d1 may be set at approximately 2 inches. Also, a third hollow pin may be positioned at a different distance from the two hollow pins to form an isosceles triangle arrangement. In this way, when the therapy device 100 is moved along the muscle, with the two hollow pins 140 spanning laterally across the muscle, the third hollow pin 140 may target the middle of the muscle.

Consideration of the distance between the hollow pins 140 may also depend on how the magnetic fields of the hollow pins 140 are intended to interact, if at all. It may be desired that the hollow pins 140 be spaced far enough away from one another that the magnetic fields of the magnetics among the hollow pins 140 do not interact with each other. In other embodiments, the hollow pins 140 may be set at a predetermined distance for the magnetic fields of the magnets 150 of the hollow pins 140 to overlap.

Additionally, beyond distance spacing between the hollow pins 140, the hollow pins 140 may also be arranged at various angles relative to the device axis X. In the embodiment of FIG. 2, the hollow pins 140 are arranged vertically aligned with the device axis X. However, the hollow pins 140 may be mounted at an angle relative to the device axis X. For example, the mounting bore 136, as shown in FIG. 4, of the mounting portion 130 may be at an angle relative to the device axis X, such that the screw member 152 is at an angle relative to the device axis X when fastened to the mounting bore 136. The angle of the mounting bore 136 may be from 1 degree to 89 degrees relative to the device axis X. More specifically, the angles may be between 15 degrees to 60 degrees. The angle of the mounting bore 136 may be 45 degrees.

In combination with the orientation of the magnet 150 enclosed by the hollow pin 140, the various angles of an arrangement of hollow pins 140 may be used for arranging a predetermined overlap or distance of the magnetic fields of the magnets 150. The various angles may be from 1 degree to 179 degrees relative to the mounting portion 130. More specifically, the various angles may be between 45 degrees to 135 degrees. The angle of the hollow pins 140 may be 90 degrees. For example, by having radially outwardly arranged hollow pins 140 from the mounting portion 130, a treatment area covered by the contact portion 142 of the hollow pins 140 may be larger than the area covered by the mounting portion 130. This may allow for a smaller therapy device 100 in terms of the holding portion 100, neck portion 120, and mounting portion 130.

In one or more embodiments, the hollow pins 140 are made of a material such as but not limited to a metallic material, a composite material, a non-metallic material or any other material, as per design feasibility and requirement. In some embodiments, the hollow pins 140 may be made of hypoallergenic materials such as but not limited to surgical steel, titanium and the like. In some embodiments, the material of the hollow pins 140 may be characterized with high magnetic conductivity. In other words, the material of the hollow pins 140 may be selected to ensure transmission of a predetermined magnetic flux from the magnet 150 to the treatment area of the patient during use.

In one or more embodiment, the hollow pins 140 are made of steel. It is also contemplated that when the hollow pins 140 are made of steel or other thermally conductive materials, the hollow pins 140 may be attached to a heating element or a cooling element (e.g., thermoelectric cooler). The heating element heat the hollow pins 140 and the contact portion 142 of the hollow pin. In this way, magnetic flux from the magnet 150 as well as the heat generated from the heating element may be transmitted to the treatment area, thereby providing comfort to the patient and accelerating treatment (e.g., draw out the toxins from the treated tissue or muscles). The cooling element may transfer heat away from the hollow pins 140 and the contact portion 142 of the hollow pin. In this way, magnetic flux from the magnet 150 as well as the drawing of heat away from the treated area of the tissue/muscle due to the cooling element may provide comfort to the patient and accelerate treatment (e.g., reduce swelling and inflammation from the treated tissue or muscles).

Additionally, it is also contemplated with respect to the embodiment shown in FIG. 2 that the hollow pin 140 and the mounting portion 130 may be fabricated from a unitary material. The shape may be formed by various methods including forging, casting, or machining. When the mounting portion 130 and the hollow pin 140 are fabricated from a unitary material, a bore hole could be machined into the hollow pin 140 from the top surface 132 of the mounting portion 130 in order to position the magnet 150 into the hollow pin 140. The bore hole may be partially threaded to allow for positioning of a resilient member 154 and a screw member 152, the screw member 152 threadedly engaging the bore hold and retaining the magnet 150. In other embodiments, the magnet may be fixed inside the bore hole by means of an adhesive or resin. In other embodiments, the magnet may be sized for a press fit into the bore hole without need for additional fixation.

In one embodiment, integral formation of the hollow pin 140 and the mounting portion 130 may be done for example with injection molding. In such a case, a magnet could be positioned inside a mold for both the mounting portion 130 and the hollow pin 140 such that both the mounting portion 130 and the hollow pin 140 may be integrally formed.

Methods of manufacturing the therapy device 100 of FIGS. 1-5 and as described above include forming by machining, injection molding, 3-D printing, forging, or casting of the holding portion 110, the neck portion 120, the mounting portion 130, and the hollow pin 140. One or more methods may include forming the holding portion 110, the neck portion 120, and the mounting portion 130 separately or integrally. In embodiments of the method where at least one of the holding portion 110, the neck portion 120, are the mounting portion 130 is formed separately from the others, the method includes affixing the separate component to the others.

One or more methods of manufacturing may include placing a magnet 150 inside a bore hole 144 of the hollow pin 140. One or more methods may include placing a resilient element 154 inside the bore hole 144, the resilient element 154 being proximal to the magnet 150. One of more methods may include fastening a screw member 152 to a bottom surface 134 of the mounting portion 130, a portion of the screw member 152 projecting from the bottom surface 134. Some embodiments of methods include fastening the hollow pin 140 to the screw member 152, with the magnet 150 and the resilient element 154 being retained in the bore hole 144 of the hollow pin 140.

Methods of use for the therapy tool 100 may include various finger hold configurations depending on the size and shape of the holding portion 110 and the neck portion 120. By utilizing magnetic flux instead of physical massaging techniques, the therapy tool 100 may be used to stimulate the lymphatic system with a range of 0 pounds to less than approximately five pounds, of force on the treatment area. As such, the physical discomfort from conventional physical massaging techniques may be avoided.

Methods of use may include a user gripping a therapy device 100 of FIGS. 1-5 by grasping the neck portion 120 with two fingers with the neck portion 120 between the two fingers. By squeezing the two fingers together, the user may hold and maneuver the therapy device 100. Additionally, if the user grasps the neck portion 120 with two fingers with the user's palm side facing in the proximal direction of the therapy device 100, the user may also place their thumb over the top surface 112 of the holding portion 110 for additional stability.

In embodiments where the therapy device 100 is larger and the top surface 112 is sized to fit in the palm of a user, methods of use may provide that the user may grip around the holding portion 110 and hold the neck portion 120 with up to fingers.

After gripping of the therapy device 100, the user may position the therapy device 100 over a target treatment area. The user may move the therapy device 100 in a reciprocating motion over the treatment area. For example, if the target area is along a muscle such as a bicep, the user may move the therapy device 100 back and forth along the length of the bicep muscle.

However, it is also contemplated that the user may move the therapy device 100 along a predefined motion pattern around the treatment area. For example, on a back of a patient, the user may move in a predefined motion pattern such as a figure eight, circle, square, or other necessary pattern.

It is also contemplated that the user may use the therapy device 100 for intervals of approximately 1 minute to 2 hour. More preferably, the user may use the therapy device 100 for an interval of approximate of 5 minutes to 30 minutes. The user may desire to use the therapy device for 15 minute intervals. The user may use the therapy device 100 on a patient in a range of once a day to four times a day. More specifically, the user may use the therapy device 100 on a patient between once a day and twice a day. The user may use the therapy device 100 once a day on the patient. The user may use the therapy device 100 on a patient in a range of four times a day to once a month. More specifically, the user may use the therapy device 100 on a patient between twice a day and once a week. The user may use the therapy device 100 once a day on the patient.

Depending on the weight of the therapy device 100 and the positioning of the therapy device 100 relative to the patient, the user may adjust the amount of force applied on the patient through the therapy device 100 to prevent excessive force. Additionally, the magnetic flux on the patient may be reduced by having the user move the therapy device 100 away from the skin of the patient to distance the magnet 150 from the patient.

Additionally, especially for intricately contoured areas of the body, such as joints, the user may tilt and angle the therapy device 100 such that a contact portion 142 of one of the hollow pins 140 of the therapy device 100 may access the contoured treatment area. Additionally, tilting the therapy device 100 relative to the patient may adjust the magnetic flux on the patient.

Figure 7:
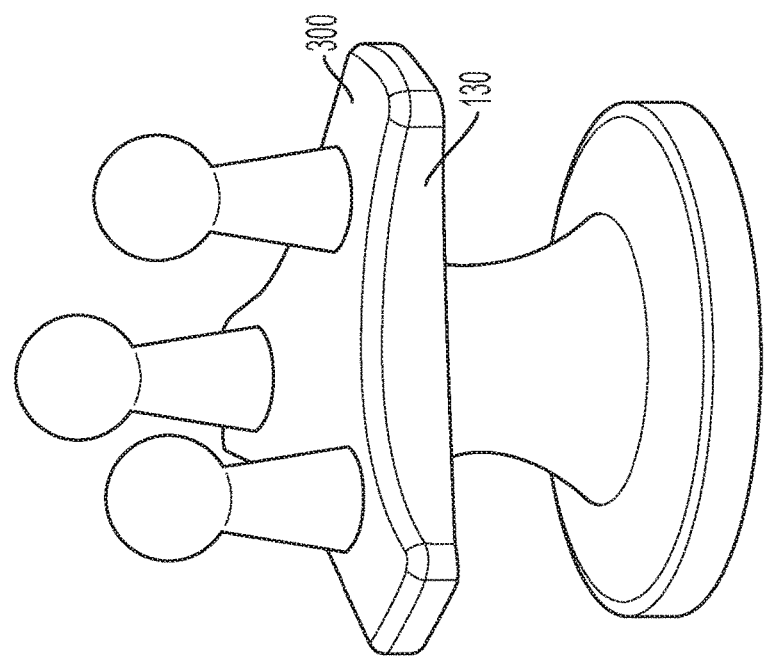
FIG. 7 shows a perspective view of the magnetic therapy device shown in FIG. 6.
Figure 6:
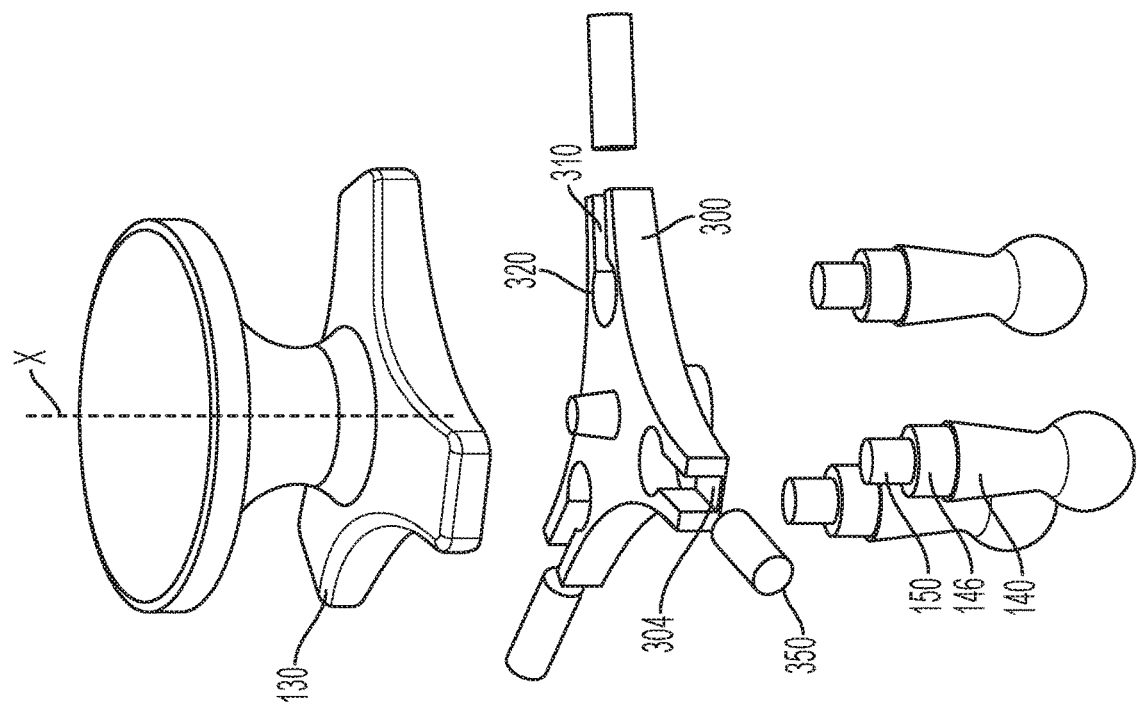
FIG. 6 shows an exploded perspective view of a variant of the magnetic therapy device shown in FIG. 1.

FIGS. 6 and 7 illustrate a variant to the first embodiment of a magnetic therapy device 100 having two sets of perpendicularly arranged magnets. FIG. 6 illustrates the embodiment from a perspective view from the top side and FIG. 7 illustrates the embodiment from a perspective view of the bottom side.

Similar to the embodiment of FIG. 1, the therapy device 100 may have a body 102 including a holding portion 110, a neck portion 120, and a mounting portion 130. The neck portion 120 is between the holding portion 110 and the mounting portion 130.

FIG. 6 shows a mounting portion 130 having a three-corner star cross-sectional shape. Alternative cross-sectional geometric shapes as viewed from a top view may be utilized for the mounting portion 130. For example, the mounting portion 130 may define a circle, a rectangle, a triangle, or a multi-point star, among other geometric cross-sectional shapes.

Additionally, on the bottom side of the mounting portion 130 is a recess 138 or cavity. The recess 138 may follow the external shape of the mounting portion 130 and be inset a certain distance from the outside edge of the mounting portion 130. The recess 138 may have a depth that is between 20% and 90% of the thickness of the mounting portion 130. In the embodiment of FIG. 6, the recess 138 has a three-corner star cross-sectional shape inset in the mounting portion 130.

In some embodiments, the recess 138 may have a cross sectional shape different from the mounting portion 130. For example, if the mounting portion is triangular or square, the recess 138 may be circular or another geometric shape.

An insert piece 300, or plate member, may correspond to the recess 138 of the mounting portion 130. When fitted into the recess 138, the plate member 300 may serve as the bottom surface 134 of the mounting portion 130 as shown in FIG. 7. In some embodiments, the insert piece may be sized and shaped to be retained in the recess 138 by a press fit. In some embodiments, the insert piece may be clearance fit into the recess 138 and held in place by an adhesive or a snap clip interface on the mounting portion 130.

In the embodiment of FIG. 6, the insert piece 300 may have a three-corner star cross-sectional shape corresponding to the recess 138. Each arm 302 of the insert piece 300 may have a side opening 310 and an axial opening 320. In some embodiments, the side opening 310 and the axial opening 320 are connected together. The side opening 310 may be a groove cut into the arm 302 from the tip end of the arm towards the center of the insert piece 300. The groove may be sized and shaped for receiving a magnet 350. Additionally, there may be a bottom wall 304 to retain the magnet 350 when the insert piece 300 is mated with the mounting portion 130. In this way, the magnet 350 may be retained near the tip end of the arm, and therefore an outer edge of the mounting portion 130 when the insert piece 300 is mated with the mounting portion 130.

The axial opening 320 may be a bore generally aligned with the device axis X and perpendicular to the side opening 310. In other embodiments, the axial opening 320 may be at an angle relative to the device axis X to provide for angled mounting of the hollow pins 140 similar to the alternative embodiments for angled mounting as described above for FIGS. 1-5. The axial opening 320 may be sized for fitment with a hollow pin 140.

In some embodiments, the hollow pin 140 may have a fitment portion 146 that is sized to fit with the axial opening 320. The fit may be a press fit or a clearance fit for securing with an adhesive. In some embodiments the fitment portion 146 is a region of the hollow pin 140 with a stepped down, smaller diameter. The hollow pin 140 may have a bore hole 144 for fitment of a magnet 150. In this way, the arrangement of the magnets 150 in the hollow pins 140 of the therapy device 100 may be perpendicular to the magnets 350 of the insert piece 300. In this way, the magnetic field of the magnets 350 of the insert piece 300 may overlap with the magnetic field of the magnets 150 of the hollow pins 150 and thereby supplement the magnetic flux transferred to the treatment area of the patient to improve therapeutic efficiency of the therapy device 100.

Alternatively, the magnets 350 and the magnets 150 do not have to be perpendicular to each other. Instead, they may be set at various angles or even aligned with one another for the desired magnetic flux.

Additionally, with the addition of the magnets 350 enclosed between the mounting portion 130 and the insert piece 300, the corners of the mounting portion 130 may thus also be used for magnetic massaging in addition to the contact portions 142 of the hollow pins 140.

In addition to the methods of assembly of the embodiment of FIG. 1, the embodiment of FIG. 6 may further include forming the insert piece 300 with side openings 310 and axial openings 320. One or more methods may include fixing magnets 350 in the side openings 310. One or more methods may include coupling the hollow pins 140 to the axial openings 320 of the insert piece 300. One or more methods may include attaching the insert piece 300 to the mounting portion 130.

In addition to the methods of use of the embodiment of FIG. 1, the embodiment of FIG. 6 also allows for the user to target a treatment area of a patient with the side edge of the mounting portion 130, which encloses a magnet 350. In embodiments where the mounting portion 130 may have corners, such as in the three-corner star shape, the corner may be applied to the targeted treatment area and provide access to intricately contoured regions of the patient. Additionally, the corner may provide a different contact shape than the contact portion 142 of the hollow pin 140 for differing contact sensation for the patient.

In exemplary embodiments of the above embodiments of FIGS. 1-7, the therapy device 100 may be configured as a face massager with a body diameter ranging from about 2 inches to 3 inches.

Figure 8:
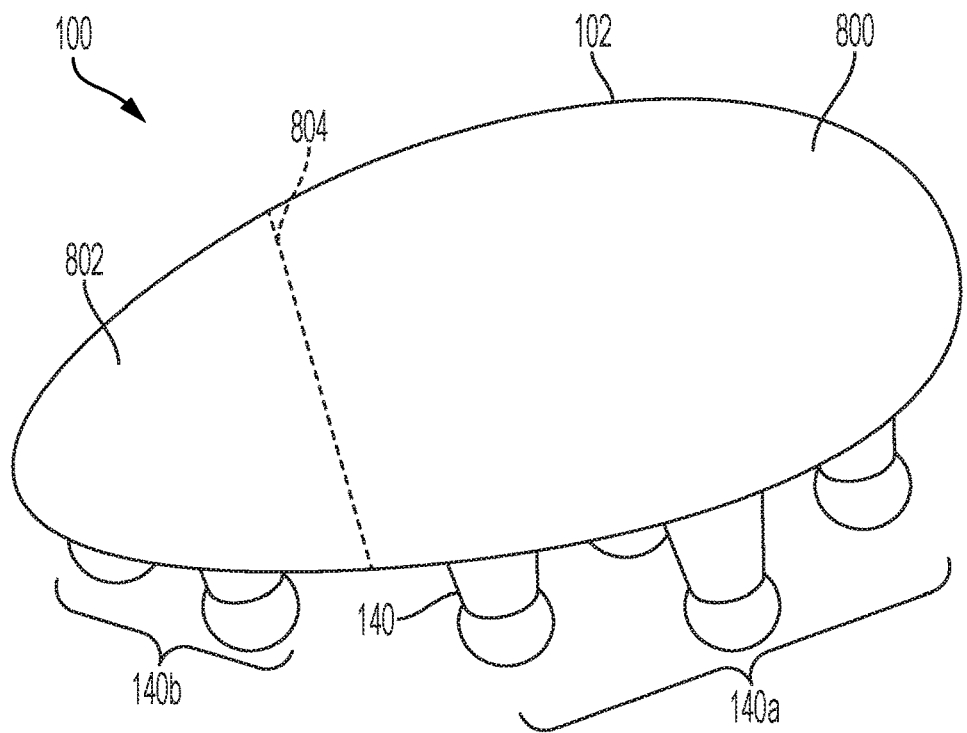
FIG. 8 shows a perspective view of a second embodiment of the therapy device.

FIG. 8 illustrates a perspective view of an embodiment of a therapy device 100 with a body 102 having a major section 800 and peripheral section 802.

In one or more embodiments, the body 102 may be a unitary teardrop shape that serves as the mounting portion 130 as well as a holding portion. As such, the body 102 may be a monobloc construction. Alternatively, the body 102 may comprise separate a holding portion 110 defining the teardrop shape and an insert piece serving as a mounting portion 130 similar to the embodiment of FIG. 9 below.

The teardrop shape of the body 102 may be an elongate shape with a first end that is rounded and a second end that is more pointed, or has a smaller radius of curvature, than the first end. As such, the teardrop shape may be thought of in two sections, the major section 800 including the first end and a peripheral section 802 including the second end. The major section 800 and the peripheral section 802 may be understood as being separated by an intermediary divide 804.

The major section 800 may have a larger length and a larger average width than the peripheral section 802. The average width of the major section 800, at portion, may be from approximately 1 inches to 6 inches. More specifically, it may be 2 inches to 4 inches. In one example, the average width of the major section 800 may be approximately 2.5 inches. On the bottom side of the body 102 are hollow pins 140 for both the major section 800 and the peripheral section 802. The bottom side of the body 102 may include mounting bores for fastening of the hollow pins 140. The hollow pins may be understood as enclosing a magnet 150 as in the previous embodiments. The major section 800 may have a higher number of hollow pins in a major grouping 140a than the peripheral section 802, which has a lower number of hollow pins in a peripheral grouping 140b.

The major section 800 has a larger surface area and the major grouping 140a may contact a larger surface area of the treatment area, thereby alleviating necessity of re-positioning the device for treating the treatment area. The major grouping 140a may be configured to engage with a portion on a patient's body such as but not limited to a shoulder portion, a thigh portion and the like, which are characterized by large areas of substantial flat surfaces. The major grouping 140a may ensure that the user may engage with a substantial portion of the treatment area in a single movement, thereby minimizing the necessity for repeated use of the device 100. In an exemplary embodiment, the major grouping 140a may have six hollow pins 140.

The peripheral section 802 is smaller and may therefore be used on more intricate regions of the treatment area, such as a joint. The average width of the peripheral section 802, at portion, may be approximately 0.5 inches to 5 inches. More specifically, it may be 1.5 inches to 3.5 inches. In one example, the average width of the peripheral section 802 may be approximately 2 inches. The peripheral grouping 140b may be configured to engage with a portion on the patient's body characterized with uneven or irregular surfaces. This configuration of the therapy device 100 ensures access to intricate regions of the treatment area, thereby minimizing the need for a supplemental device for accessing the intricate regions. In an exemplary embodiment, the peripheral grouping 140b may have two hollow pins 140. From the arrangement relative to the first end and the second end, it may be understood that the major grouping 140a is on an opposed portion from the peripheral grouping 140b.

Alternative numbers of hollow pins 140 in the major grouping 140a and the peripheral grouping 140b may be provided.

In addition to the methods of use described above with respect to FIGS. 1-7, the therapy device of FIG. 8 may be grasped in the palm of a user. When the user holds the therapy device with the first end between the thumb and the index finger, the user may easily operate the major section 800 across a treatment area. When the user holds the therapy device with the second end between the thumb and the index finger, the user may also provide a small amount of tilting such that the hollow pins 140 of the peripheral grouping 140b may access intricately contoured regions of the patient.

Figure 9:
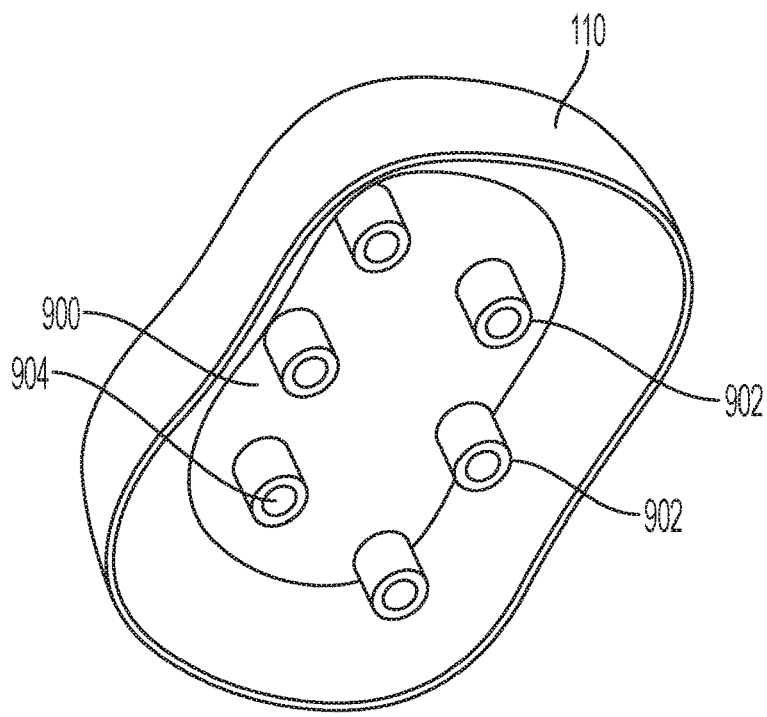
FIG. 9 shows a perspective view of a variant of the holding portion of the body shown in FIG. 8.
Figure 10:
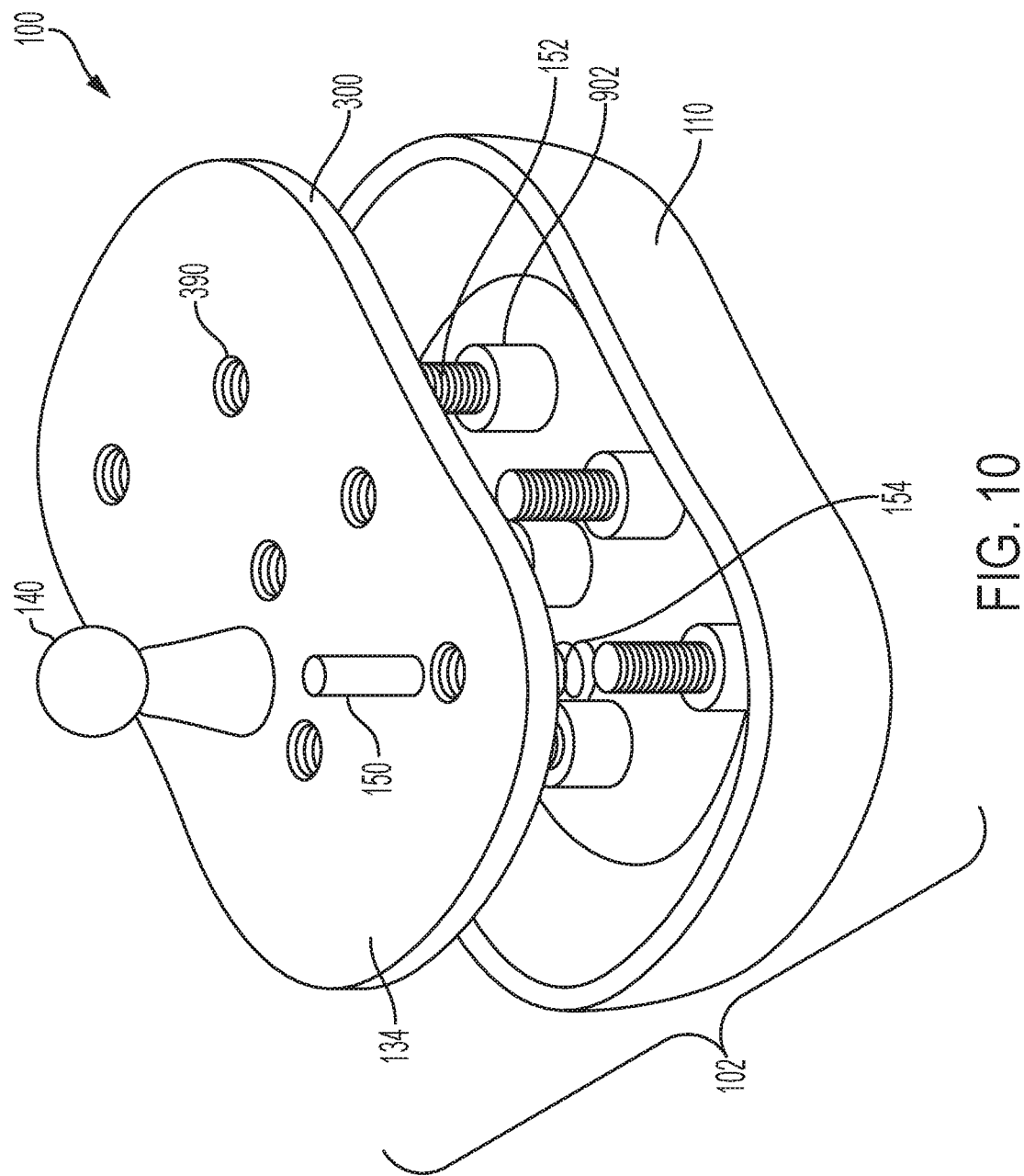
FIG. 10 shows an exploded perspective view a variant of the therapy device shown in FIG. 8.

FIGS. 9 and 10 illustrate an embodiment of a therapy device where body 102 is formed for two parts with a holding portion 110 and an insert piece 300, which serves as a mounting portion 130. FIG. 9 illustrates a perspective view of the holding portion 110 of the body from a bottom side view. The holding portion 110 may have a rectangular cross sectional shape, or parallelogram, similar to a bar of soap. On the bottom side of the holding portion 110 is a recess 900. The recess may have at least one mounting standoff 902. In the exemplary embodiment, there are six mounting standoffs 902. The mounting standoffs may have a mounting bore 904 for accepting a screw member 152. The mounting bore 902 may have threads for fastening the screw member 152.

FIG. 10 illustrates an exploded perspective view of the therapy device 100 from the bottom side view. The body 102 may include an insert piece 300. The insert piece 300 may correspond to the shape of the recess 900 and serve as a bottom surface 134 of the body 102 when assembled with holding portion 110. The insert piece 300 may have through holes 390 for the screw members 152 to pass through. In the assembled state, the screw members 152 may fasten to the mounting standoff 902 in the recess 900 of the body 102 and extend outward from the body past the insert piece 300.

Similar to the above described embodiments, a hollow pin 140 may fasten to the screw member 152. Enclosed inside the hollow pin 140 may be a magnet 150 in a bore hole of the hollow pin 140. A resilient member 154 may be positioned in the bore hole between the magnet 150 and the screw member 152.

In exemplary embodiments of the above embodiments of FIGS. 8-10, the therapy device 100 may be configured as a body massager with a length of the arrangement of hollow pins 140 ranging from approximately 2 inches to 5 inches. More specifically, the length may range from 3 inches to approximately 3.6 inches. In one example, the length may be approximately 3.3 inches.

Figure 11:
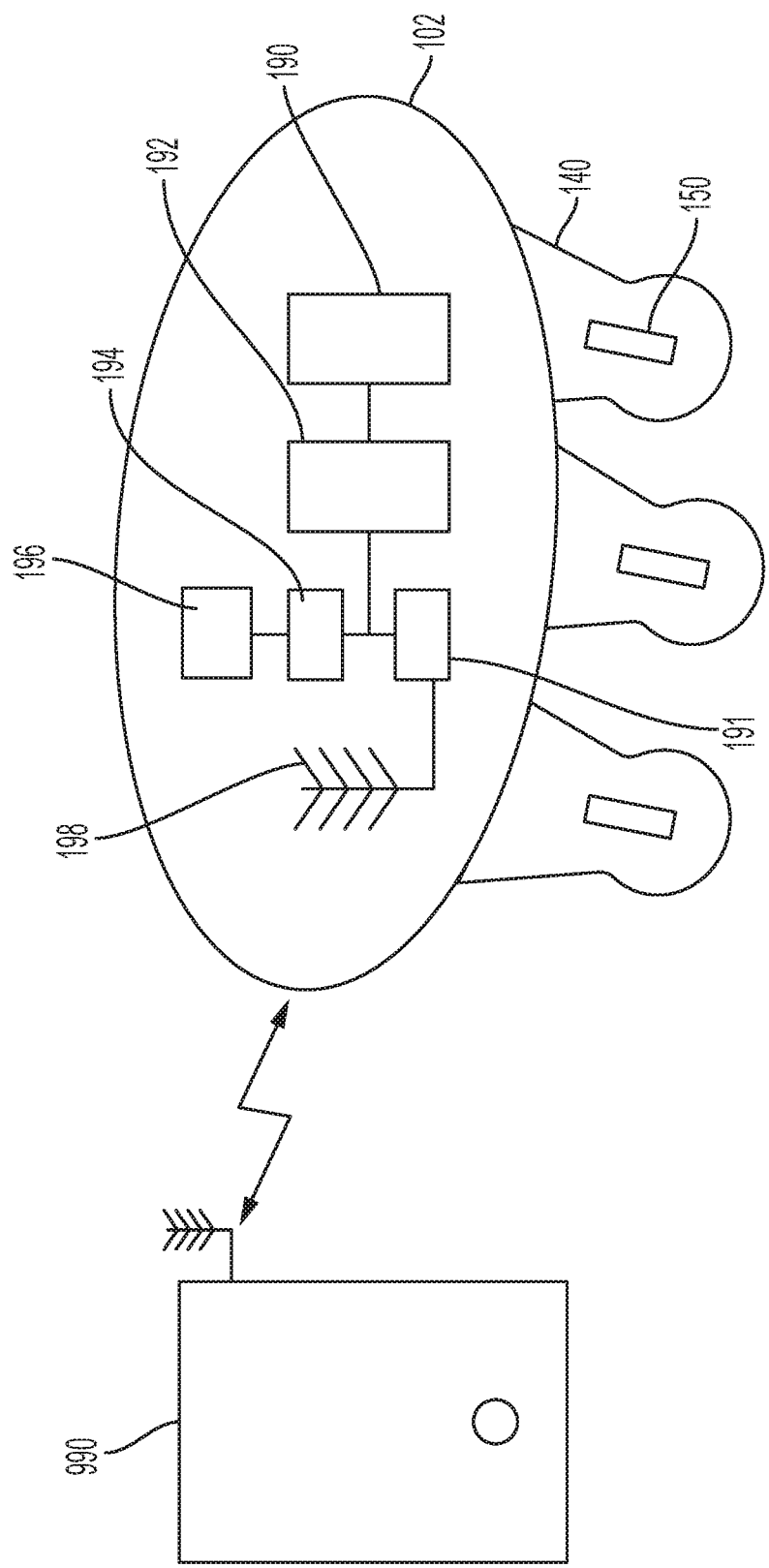
FIG. 11 shows embodiment variant of the magnetic therapy device shown in FIG. 8 having electronic components.

FIG. 11 illustrates an embodiment of a therapy device 100 further comprising electronic functionality. The therapy device 100 may be one of the above described embodiments or a variation as would be understood in view of the present disclosure. The therapy device 100 may further include a heater and cooler 190, a vibration mechanism 192, a controller 191, a rechargeable battery 194, a wireless charger 196, and an antenna 198.

The heater and cooler 190 may generate thermal heating and transfer the heat to the hollow pins 140 of the therapy device. Alternatively, the heater/cooler 190 may draw heat away from the hollow pins 140. The heater and cooler 190 may directly contact the hollow pins 140 or they may be coupled to the hollow pins 140, such as by way of a thermal pipe. In this way, the heater and cooler 190 may provide a heated or cooled hollow pin 140 for contact with the treatment area of the patient to apply heat to draw toxins out and to cool down the treatment area to reduce swelling and inflammation. The heater and cooler 190 may be controlled by a controller 191.

The controller 191 may comprise a processor to activate and deactivate the heater and cooler 190, the vibration mechanism 192, and the wireless charger 196. The controller 191 may also include a computer readable storage medium to store program code executable by the processor to activate and deactivate the heater and cooler 190, the vibration mechanism 192, and the wireless charger 196.

The vibration mechanism 192 may be provide for vibration of the therapy device 100. In some embodiments, the vibration mechanism 192 may include a vibration motor with a weight on the motor shaft to cause vibration during running of the motor.

The wireless charger 196 may charge an onboard rechargeable battery 194. The wireless charger 196 may be of one of the Qi™ or PowerMat™ wireless charging standards. Alternatively, the wireless charger 196 may be of another type of wireless charging standard. Alternatively, the therapy device may use a conventional power plug for charging.

The controller 191 may send and receive signals through an antenna 198. In embodiments, the therapy device 100 may wirelessly interface with a mobile app for a mobile device 990.

For example, in some methods of use, a user may use the mobile app to turn on or turn off the vibration mechanism 192 or the heater and cooler 190. In some methods of use, the use may use the mobile app to view the battery status of the rechargeable battery 194 of the therapy device 190. In some methods of use, the mobile app may provide a timer feature to log the amount of time that the therapy device 190 has been used on a patient.

Figure 12:
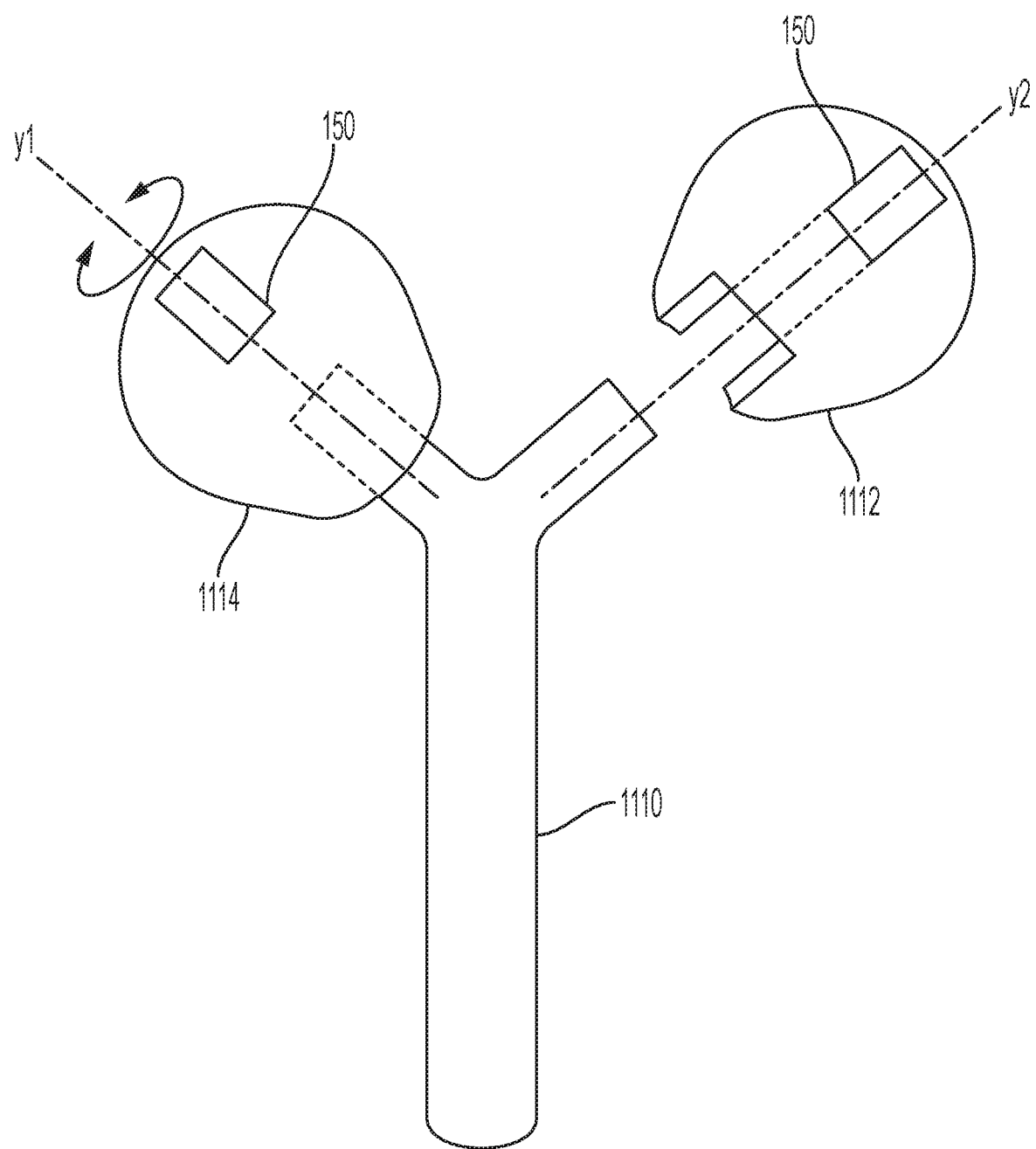
FIG. 12 shows a fourth embodiment of the therapy device utilizing rollers with magnets.

FIG. 12 illustrates an embodiment of a therapy device 1110 utilizing rollers with magnets. The therapy device 1110 may have at least one roller 1112 configured to rotate about an axis Y2. It is contemplated that the therapy device 1110 may be useful for facial rolling, such as for wrinkle removal. The details of a facial roller are set forth in a LaLaBEAUTY 3D facial roller as available from Rakuten on Oct. 2, 2018, are hereby incorporated by reference.

In the exemplary embodiment, the therapy device 1110 may have two rollers 1112, 1114 each rotatable about respective axes Y2 and Y1. The rollers 1112, 1114 may be rotated by one or more motors enclosed in the therapy device. The rollers 1112, 1114 may have a diameter ranging from approximately 0.5 inches to 3 inch. More specifically, the rollers 1112, 1114 may have a diameter approximately from 1 inch to 2 inches.

The rollers 1112, 1114 may be generally spherical. In a distal portion away from the therapy device, each of the rollers 1112, 1114 may enclose a magnet 150. The roller 1112, 1114 may have a bore for fitment of the magnet 150 or the roller could be formed around the magnet by methods such as injection molding. In this way, the rollers 1112, 1114 may both roll as well as serve to act on the lymphatic system.

It is also contemplated that the rollers 1112, 1114 may have different geometric shapes from spherical, such as ellipsoid or cylindrical.

It is also contemplated that variants may have different numbers of rollers from one-roller and two-roller therapy devices 1110. Variants of the therapy device 1110 may include three-roller variants, four-roller variants, five-roller variants, or variants with even high numbers of rollers. Variants of more than one roller may have the rollers arranged angled relative to one another. Variants of more than one roller may have the rollers arranged parallel to one another and defining a set of rollers to flatly contact the patient's skin.

In variants of the embodiment shown in FIG. 12, the therapy device 1110 may be understood as being of other categories of facial rollers. The embodiment of FIG. 12 may be understood as a vertical type roller where the rollers 1112, 1114 rotate around a shaft of the therapy device. Other categories of facial rollers may include horizontal rollers where the rollers may be understood as rotating about an axis parallel to the skin. In some variants of horizontal rollers, the therapy device 1110 may hold an individual roller at two opposed portions of the roller, so that the roller spins around an axis defined by where the therapy device 1110 holds the roller.

Methods of use of the variant shown in FIG. 12 include placing at least one of the rollers 1112, 1114 in contact with the patient's skin. The user may move the rollers 1112, 1114 along a predefined motion pattern. In use, the user may apply these rollers to the skin such that the axis of rotation of the rollers points towards the skin. The user may also tilt the rollers relative to the skin, from an angle ranging from 1 degree to 179 degrees. More specifically, the angle that the rollers may be tilted relative to the skin may from 45 degrees to 135 degrees. The angle of the tilt of the rollers relative to the skin may be 70 degrees.

Additional combinations of methods of making therapy devices and of using the therapy devices as described herein are within the scope of the present invention.

The detailed description set forth above in connection with the appended drawings is intended as a description of the presently preferred embodiments of therapy devices with magnets provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. Furthermore, it is understood and contemplated that features specifically discussed for one therapy device embodiment may be adopted for inclusion with another embodiment, provided the functions are compatible. As denoted elsewhere herein, like element numbers are intended to indicate like or similar elements or features.

The term "user" used throughout the disclosure may refer to a person performing the treatment or massaging procedure. The term "patient" used throughout the disclosure may reference to a person or an animal on whom the treatment or massaging procedure is being performed. In the present context, the massaging procedure may be carried out using the magnetic therapy device defined in the disclosure. In some cases, the user may perform the massaging procedure on themselves, thereby making the user and the patient the same person.

Reference in this specification to "one embodiment" or "an embodiment" means that a particular feature, structure, or characteristic described in connection with the embodiment is included in at least one embodiment of the present disclosure. The appearance of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

What is claimed is:

1. A magnetic therapy device for treating a body part, comprising:
   a body including:
      a holding portion for gripping by a user's hand;
      a mounting portion attached to the holding portion;
      first, second and third pins attached to the mounting portion, the first, second and third pins extending away from the holding portion of the body, the first pin having a first cavity, the second pin having a second cavity, the third pin having a third cavity; and
   first, second and third magnets, the first magnet disposed within the first cavity of the first pin, the second magnet disposed within the second cavity of the second pin, the third magnet disposed within the third cavity of the third pin.

2. The device of claim 1 wherein the first, second and third magnets have polarities, and the polarities of the first, second and third magnets are oriented in a first direction and are parallel to each other.

3. The device of claim 2 wherein the first, second and third magnets have magnetic north poles, and the magnetic north poles of the first, second and third magnets are directed in the first direction.

4. The device of claim 1 wherein the first, second and third magnets have polarities, and the polarities of the first, second and third magnets are oriented at skewed angles with respect to each other.

5. The device of claim 1 wherein the first, second and third magnets are equidistantly spaced apart from each other less than or equal to 1 to 3 inches.

6. The device of claim 1 wherein the pins are fabricated from surgical steel or titanium.

7. The device of claim 1 further comprising:
   a heater disposed within the body for providing heat to surfaces of the pins configured to contact the body part being treated;
   a vibrator disposed within the body and configured to provide vibration to the body part being treated; and
   a battery disposed with the body and electrically connected to the heater and the vibrator to power the heater and the vibrator.

8. The device of claim 7 further comprising a cooler disposed within the body for drawing heat away from the surfaces of the pins which are configured to that contact the body part being treated.

9. The device of claim 1 wherein the pins comprise rollers.

10. The device of claim 1 wherein the body has an upper dome shaped surface to ergonomically interface with a palm of a user.

11. The device of claim 1 further comprising a neck portion which connects the holding portion and the mounting portion, the neck portion being narrower compared to the holding portion and the mounting portion, the neck portion being sufficiently narrow so that a person's index and middle fingers can be placed on opposed sides of the neck portion.

12. The device of claim 1 wherein the pins are removably attachable to the mounting portion to interchange the magnets disposed in the cavities of the pins with stronger or weaker magnets.

13. The device of claim 1 wherein springs are disposed within the cavities of the pins to stabilize the magnets within the cavities of the pins.

14. A method of treating a body part with a magnetic field, the method comprising the steps of:
   touching two pins of a magnetic therapy device on a surface of a body part being treated;
   allowing two magnetic fields of two magnets disposed inside the two pins which intersect to penetrate a location of the surface of the body part being treated at the same time; and
   moving the intersecting magnetic field over the surface of the body part being treated.

15. The method of claim 14 wherein the moving step further comprises the step of moving the intersecting magnetic field in a FIG. 8 motion on the surface of the body part being treated.

16. The method of claim 14 further comprising the step of allowing a weight of the device to apply pressure to the surface of the body part being treated.

17. The method of claim 14 wherein the moving step is performed for 15 minutes.

18. A magnetic therapy device for treating a body part, comprising:
   a body including:
   a holding portion for gripping by a user's hand;
   first and second pins adjacent to the holding portion, the first and second pins extending away from the holding portion of the body, the first pin having a first cavity, the second pin having a second cavity; and
   first and second magnets, the first magnet disposed within the first cavity of the first pin, the second magnet disposed within the second cavity of the second magnet.

* * * * *